United States Patent [19]
Abdel-Rahman

[11] Patent Number: 5,920,072
[45] Date of Patent: Jul. 6, 1999

[54] IONIZATION DETECTOR

[75] Inventor: Mahmoud F. Abdel-Rahman, West Grove, Pa.

[73] Assignee: Hewlett-Packard Co., Palo Alto, Calif.

[21] Appl. No.: 08/940,511

[22] Filed: Sep. 30, 1997

[51] Int. Cl.$^6$ .............................. H01J 47/02; G01T 1/18; G01N 27/64
[52] U.S. Cl. ...................... 250/384; 250/379; 250/381; 250/382; 250/385.2; 324/469
[58] Field of Search ..................................... 250/374, 379, 250/380, 381, 382, 384, 385.1, 389; 324/464, 469

[56] References Cited

U.S. PATENT DOCUMENTS

| | | | |
|---|---|---|---|
| 3,361,907 | 1/1968 | Gregory | 250/389 |
| 4,780,284 | 10/1988 | Lovelock | 422/83 |
| 5,200,614 | 4/1993 | Jenkins | 250/286 |

*Primary Examiner*—Constantine Hannaher
*Assistant Examiner*—Albert Gagliardi
*Attorney, Agent, or Firm*—Mark Z. Dudley

[57] ABSTRACT

An ionization detector having an upper ionization chamber, a lower ionization chamber, and a radioactive source located in the upper ionization chamber but shielded from the lower ionization chamber by a barrier. A substantially constant fluid stream of detector gas is supplied to the upper ionization chamber so as to fill the upper ionization. The radioactive particle emitter is disposed on the periphery of the interior of the upper ionization chamber so as to generate a constant supply of alpha particles into the internal volume defined by the upper ionization chamber. The interaction of the alpha particles and the detector gas generates metastables and photons as the alpha particles traverse a portion of the volume in the upper ionization chamber. The lower ionization chamber is coupled to the upper ionization chamber so as to receive the detector gas flow and the metastables. A sample fluid is directed into the lower ionization chamber, preferably by way of a carrier gas flow supplied from an outlet end of a capillary separation column, and the metastables present in the lower ionization chamber then ionize the analyte molecules. An outlet is provided in the base of the lower ionization chamber so as to vent the combined flows of the carrier gas, sample fluid, and the detector gas. In the preferred embodiment, the carrier gas and the detector gas are helium. The barrier is interposed in the path between the radioactive source and the lower ionization chamber so as to prevent entry of the radioactive particles into the lower ionization chamber where there may ensue some interaction of the radioactive particles with analyte molecules in the lower ionization chamber. As a result, the primary mechanism for ionization of the analyte molecules is substantially restricted to an interaction of the metastables with the analyte molecules.

10 Claims, 2 Drawing Sheets

IONIZATION DETECTOR

FIELD OF THE INVENTION

This invention relates generally to detectors for analysis of an analyte present in a sample fluid; and more particularly, to ionization detectors.

BACKGROUND OF THE INVENTION

Conventional ionization detector types are known to include a helium ionization detector which typically operates by operating a beta particle emitter in a helium-filled ionization chamber. In the presence of helium, a characteristic emission of primary electrons, photons, and helium metastables will occur. A sample fluid that contains an unknown analyte is directed into the ionization chamber such that the analyte of interest may be ionized. Both the helium metastables and the photons are found to play a role in ionization of the analyte of interest. The magnitude of the ionized analyte molecules is manifested as a current that can be measured to ascertain the composition of one or more components in the analyte.

However, ample shot noise and avalanche effects have been observed in the typical helium ionization detector, due to a sufficient amount of secondary ionization that occurs in the ionization chamber as a result of direct interaction of the primary electrons, helium ions, and beta particles with the ionizable molecules in the analyte. As a result, the response of this detector is non-linear and subject to overloading (i.e., extreme peak heights). The helium ionization detector has accordingly been regarded as limited in its usefulness. The factors for this characterization include the stringent requirements for high-sensitivity operation, variations in response for selected species coupled with a lack of understanding of the conditions that generate such responses, and the belief that the detector is primarily suited for the analysis of gases that can be separated on low-bleed adsorption columns. See, for example, Ramsey and Andrawes, "The Modern Helium Ionization Detector", in *Detectors for Capillary Chromatography*, Hill, H. H. and McMinn, D. G., eds., John Wiley & Sons, 1992.

Although the design of ionization detectors continues to be an object of study in the prior art, there nonetheless exists a particular need for an ionization detector having a detector response that exhibits an improved dynamic range, lower minimum detectable level, and greater stability.

SUMMARY OF THE INVENTION

I have determined that a plurality of ionization mechanisms occur in the prior art helium ionization detectors. The variable and unpredictable nature of these plural ionization mechanisms contributes significantly to the undesirable characteristics described above. The conventional helium ionization detector suffers from the effects of the various interactions of the primary electrons, detector gas ions, and beta particles with the ionizable molecules in the analyte.

Detector response in an ionization detector is based on an accurate measurement of the ionized analyte of interest. Ionization of the analyte is preferably accomplished by a single ionization mechanism that employs metastables and photons generated from a noble gas. Restricting the ionization mechanism to one based upon the generation of metastables and photons due to the interaction of radioactive particles in a noble gas will therefore establish certain advantageous characteristics of the detector response, such as the level of lowest measurable concentration of the analyte that can be detected.

Therefore, a significant improvement in ionization detector response can be achieved by use of a radioactive source and by substantially limiting the ionization mechanism to: a) the generation of photons and metastables by interaction of a detector gas with particles emitted by the radioactive source; and b) forced interaction of such metastables with the analyte molecules.

Accordingly, the present invention is directed to a method and apparatus for limiting the analyte ionization mechanism to one primarily based upon the interaction of photons and metastables with the analyte molecules in a detection chamber in a ionization detector, and by suppressing other ionizing mechanisms, to thereby effect an improved dynamic range, lower minimum detectable level (MDL), and greater signal to noise ratio in the detector response.

A preferred embodiment of the invention includes an ionization detector having an upper ionization chamber, a lower ionization chamber, and a radioactive particle source. A substantially constant fluid stream of detector gas is supplied to the upper ionization chamber so as to fill the upper ionization chamber with detector gas. The radioactive particle source is disposed on the periphery of the interior of the upper ionization chamber so as to generate a substantially constant supply of radioactive particles into the internal volume defined by the upper ionization chamber. The interaction of the radioactive particles and the detector gas generates metastables and photons as the radioactive particles traverse a portion of the internal volume of the upper ionization chamber. A lower ionization chamber is coupled to the upper ionization chamber so as to receive the detector gas flow and the metastables. A sample fluid is directed into the lower ionization chamber, preferably by way of a carrier gas flow supplied from an outlet end of a capillary separation column, and the metastables present in the lower ionization chamber are then available to ionize the analyte molecules. An outlet is provided in the base of the lower ionization chamber so as to vent the combined flows of the carrier gas, sample fluid, and the detector gas. In the preferred embodiment, the carrier gas and the detector gas are helium and the radioactive particle source is provided in the form of an alpha particle emitter.

In a first feature of the contemplated detector, the upper ionization chamber includes a radioactive particle barrier interposed in the path between the radioactive particle source and the lower ionization chamber. The barrier limits the path of the radioactive particles to the volume defined by the upper ionization chamber, so as to block the entry of the radioactive particles into the lower ionization chamber where there may ensue some interaction of the radioactive particles with the analyte molecules that are present in the lower ionization chamber. As a result, the primary mechanism for ionization of the analyte molecules is substantially restricted to an interaction of the metastables with the analyte molecules. The contemplated detector offers greater stability and is subject to less shot noise, baseline variation, and non-linearity in the detector response, when compared to detectors of the prior art.

In another feature of the invention, a radioactive source is preferred for generating the metastables, thus effecting a very stable rate of generation of the metastables. As a result, the ionization of the analyte molecules occurs at a stable rate. In the preferred embodiment, the radioactive source is provided in the form of an alpha particle emitter. Such an emitter is advantageous because the alpha particles exhibit high energy, and the emitter is inexpensive and enhances the portability of the detector.

In another feature of the invention, the lower ionization chamber includes a high voltage signal cathode coupled to a negative potential in a high voltage supply for generating a detector signal, and such that positive analyte ions are collected.

In another feature of the contemplated detector, the upper ionization chamber optionally includes a high voltage ionization electrode coupled to a high voltage supply such that primary electrons in the upper ionization chamber are accelerated to the ionization electrode. As a result, the accelerated electrons collide with the detector gas molecules, thus improving the rate of generation of metastables in the upper ionization chamber.

In another feature of the invention, the optional high voltage ionization electrode may be coupled to a negative potential in the high voltage supply such that positive detector gas ions are collected and thus prevented from entry in the lower ionization chamber where they may be subject to collection by the signal cathode.

In another feature of the invention, a detector gas other than helium may be selected from the group of nobles gases and substituted for the detector gas and the carrier gas. Preferred choices of a replacement gas are argon or xenon.

In another feature of the invention, the ionization detector may be converted for use as an electron capture detector by continuous injection of a stream of methane gas into the lower ionization chamber.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

The apparatus and methods of the present invention may be employed in particular to improve the operation of a ionization detector for detection of an analyte that may be present in a variety of sample fluids. Gases are the preferred sample fluids according to the practice of the present invention, and therefore the following description of the invention will include a description of the arrangement, construction, and operation of a novel ionization detector for use in a gas sample analytical system. One particular application of the contemplated ionization detector is in a chromatographic analytical system (hereinafter, a chromatography; however, other applications such as process sampling systems, gas leak detection systems, air quality monitoring systems, and the like are contemplated.

The preferred operation of the contemplated ionization detector with respect to a conventional gas chromatograph may be understood as follows. In a chromatographic chamber separation of a given sample fluid, a sample fluid is injected with a pressurized carrier gas into a separation column and the column effluent is directed as a fluid stream into the ionization detector. One or more pneumatic manifold assemblies are envisioned, each of which serves in part to control and redirect a plurality of gas flows, including the carrier gas and the detector gas. Accordingly, the pneumatic manifold may be operated to effect a modulation of the aforementioned gas flows, and in particular to supply a modulated supply of detector gas flow to the ionization detector described herein.

As described herein, the preferred embodiment operates with a "carrier gas" and a "detector gas" that are preferably selected from a group of gases known as the noble gases. The carrier gas is preferably selected from a range of known gases having a higher ionization potential than the excitation potential of the selected detector gas. The preferred selection of detector gas and carrier gas is helium, but the selected detector gas and carrier gas may be another noble gas, such as argon or xenon. The term "metastable" refers to an excited atom of detector gas; in the preferred embodiment, the detector gas is helium and the metastable is a helium metastable.

Figure 1:
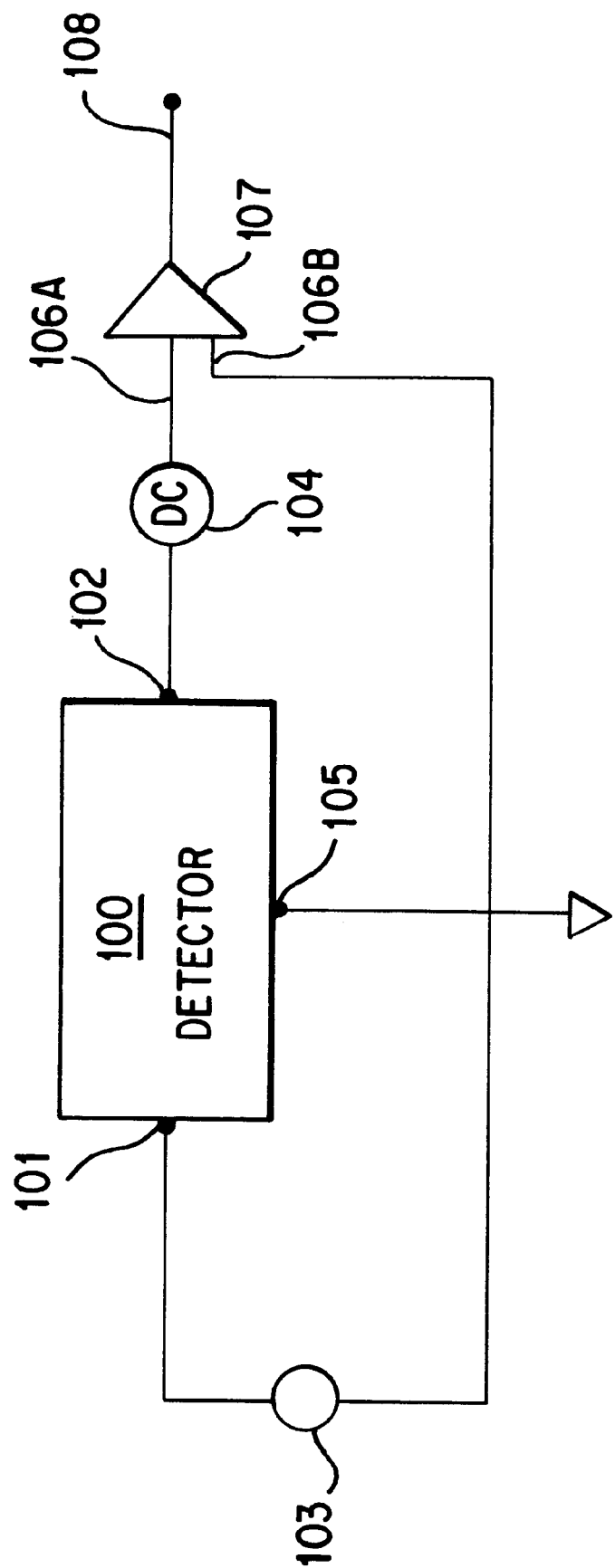
FIG. 1 is a simplified schematic view of a ionization detector constructed according to the present invention.

As illustrated in FIG. 1, a preferred embodiment 100 of a ionization detector constructed according to the invention includes an ionization chamber cathode connector 101 connected to a high voltage supply 103. The detector further includes a signal cathode connector 102, a signal bias voltage supply 104, and a common connector 105 (which is suited for coupling the body of the detector 100 to a ground potential). Differential inputs 106A, 106B in an electrometer 107 may be connected to the signal bias voltage supply 104 and the common connector 105 so as to provide a detector output signal on a detector output signal line 108 for measuring the current passing between the signal cathode connector 102 and the common connector 105.

Figure 2:
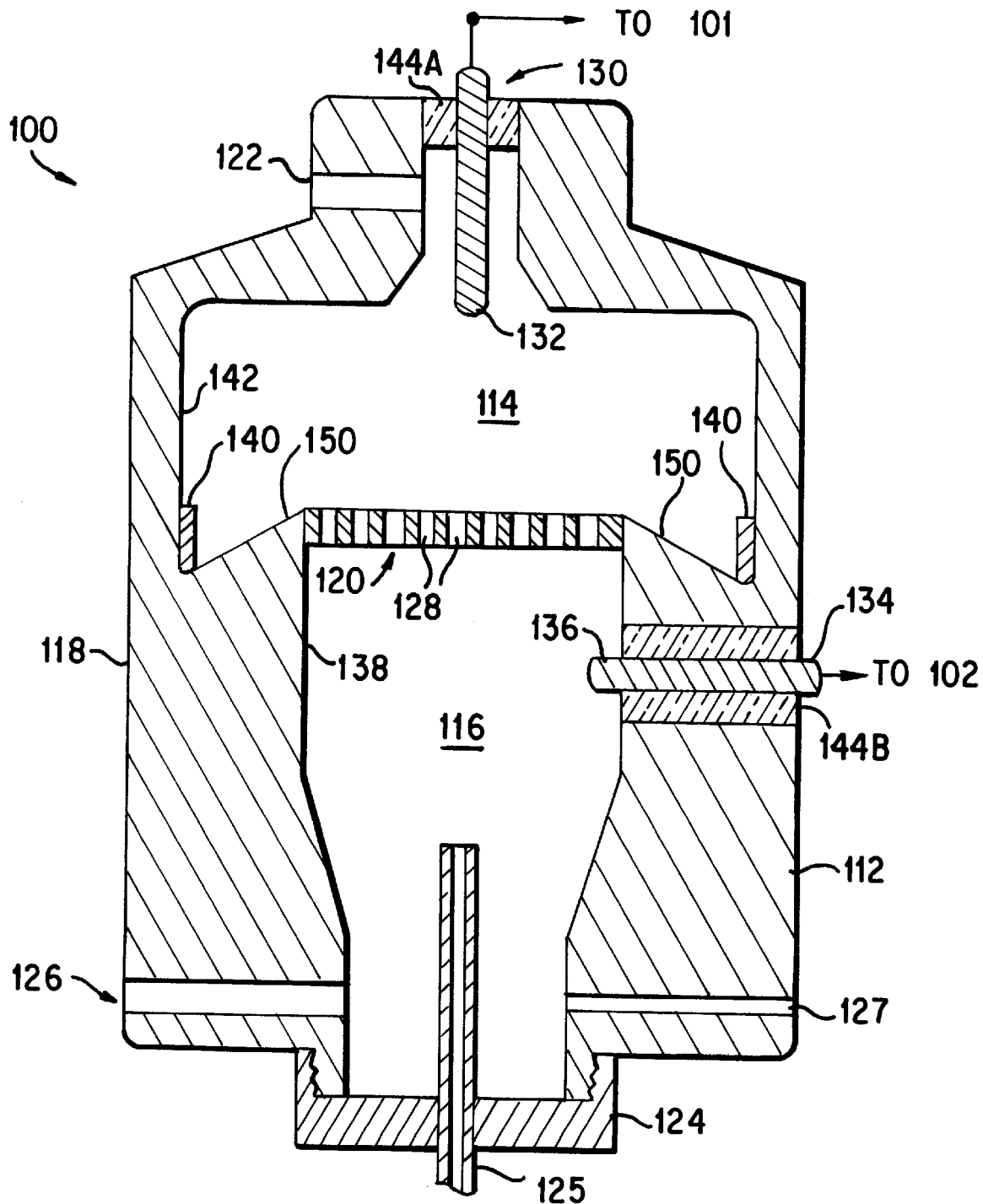
FIG. 2 is a simplified side sectional view of a portion of the ionization detector of FIG. 1.

As illustrated in FIG. 2, the preferred embodiment 100 of the ionization detector includes a detector body 112 having a common wall 118 and first and second interior chambers preferably constructed as an upper ionization chamber 114 and a lower ionization chamber 116, respectively. The upper ionization chamber 114 and the lower ionization chamber 116 share a common interior wall 138 and an optional aperture array 120 situated therebetween. The aperture array 120 may be provided in the form of a perforated disk. The volume of the lower ionization chamber 116 is preferably in the range of 25 to 250 microliters and in some applications may be less than one microliter and as large as 1 milliliter. The body 112 includes one or more inlets 122 for admitting a controlled flow of detector gas, preferably selected as one of the noble gases such as helium, and an inlet 124 to the lower ionization chamber 116 for admitting a capillary column 125 that carries a sample fluid/carrier gas mixture that contains an analyte to be detected. In the illustrated embodiment, the sample fluid inlet 124 directs the flow of sample fluid transversely to the central axis of the lower ionization chamber 116, so as to assist in retaining the analyte molecules in the lower ionization chamber 116; however, other configurations are within the scope of the present invention. Vent outlet 126 in the lower ionization chamber 116 is also provided. An optional injection port 127 may be provided that is ordinarily sealed by suitable means (not shown) until the detector 100 is converted to use as an electron capturing detector by injection of methane gas or its equivalent into the lower ionization chamber 116 via the injection port 127.

A high-voltage source includes a first electrode assembly 130 provided in the upper ionization chamber 114. The first electrode assembly 130 includes an optional ionization electrode 132 for generating an electric field in the upper ionization chamber 114. The first electrode assembly 130 is connected, by way of an appropriate electrical connector (not shown) to a high voltage potential applied between the first electrode assembly 130 and the common wall 118.

A radioactive particle source 140 is provided in the form of a thin foil located at the bottom peripheral section of the inner wall 142 of the upper ionization chamber 114. Preferably, the source 140 is an alpha particle emitter, although the use of a beta particle emitter is also contemplated. Alpha particles are emitted into the volume defined within the upper ionization chamber 114 so as to interact with the detector gas for production of high energy detector gas molecules, described herein as metastables. In the preferred embodiment, wherein helium is selected for the detector gas, the interaction of the alpha particles and the helium gas will result in a substantially constant rate of generation of helium metastables. These metastables are swept on the detector gas flow through the optional aperture array 120 into the lower ionization chamber 116. Undesirable products of the interaction, such as positively-charged detector gas ions, are attracted to the ionization electrode 132.

A preferred embodiment of the radioactive particle source 140 includes a foil of predefined height and thickness that is attached to the inner wall 142. In a particular feature of the invention, a radioactive particle barrier 150 is configured and located in the body 122 as a sloped, annular extension of the inner wall 138 that is commensurate with the height of the radioactive particle source 140 so as to limit the path of the radioactive particle emissions to the internal volume of the upper ionization chamber 114. This barrier 150 faces the radioactive source 140 so as to block the traverse of such radioactive particles into the lower ionization chamber 116, where interaction of such radioactive particles with the analyte molecules would cause an unwanted mode of ionization of the analyte molecules.

A second electrode assembly 134 is provided in the lower ionization chamber 116. The second electrode assembly 134 includes a signal cathode 136, to be negatively charged, for generating an electric field with respect to the interior wall 138 of the lower ionization chamber 116. The signal cathode 136 preferably presents a small surface area to the lower ionization chamber 116 to avoid exposure to metastables or photons and their resulting noise artifacts. Preferably, the interior wall 138 and the common wall 118 are electrically coupled and thus are at the same potential voltage. The signal cathode 136 is provided with a negative charge by coupling through electrical connector 142 to a polarizing voltage source (supply 104 in FIG. 2). The common wall 118 may be coupled to an electrometer by an appropriate electrical connector (connector 105 in FIG. 1), so as to provide for an indication of the amount of ionized components in the analyte.

In the illustrated embodiment, the detector body 112 is preferably constructed of a one or two-part cylindrical configuration. In the illustrated embodiment, the detector body 112 may be of a one-piece, unitary construction having the upper and lower ionization chambers 114, 116 machined therein. The detector gas inlet 122, sample fluid/carrier gas inlet 124, and vent outlet 126 may suitably be passageways extending through the wall 118 of the detector body 112. A major portion of the detector body 112 itself is electrically conductive and is preferably made of metal or other electrically-conductive material.

The electrode assemblies 130, 134 are respectively fitted in circular insulating adapters 144A, 144B that are each received into the detector body 112 to seal respective bores in the portions of the wall 118 at the upper ionization chamber 114 and the lower ionization chamber 116, respectively. The adapters 144A, 144B are held in position by appropriate means (not shown). The detector gas is conducted to the inlet 122 via a suitable fitting (not shown) that may be mounted on the body 112. The capillary column 125 is fitted into the lower ionization chamber 116 via a suitable fitting integrated in the inlet 124.

The geometry of the optional aperture array 120 is preferably such that the ratio of the length to the diameter of each of the bores 128 is greater than one, and is on the order of two to five. Such geometry enhances the proximity of the lower ionization chamber 116 to the upper ionization chamber 114 and reduces the path length encountered by the metastables in their travel from the upper ionization chamber 114 to the lower ionization chamber 116. Such geometry also suppresses the migration of analyte molecules from the lower ionization chamber 116 to the upper ionization chamber 114.

The bores 128 allow the passage of detector gas from the inlet 122 into the lower ionization chamber 116 and thus towards the signal cathode 136. The upper ionization chamber 114 preferably exhibits an inverse cup-shaped section being so designed and positioned such that the desired metastables can be rapidly swept from the upper ionization chamber 114 and through the bores 128 to the lower ionization chamber 116. The lower ionization chamber 116 preferably exhibits a cone-shaped section being configured such that the metastables are dispersed in the sample fluid/carrier gas mixture that is present in the lower ionization chamber 116. Upward flow of the sample fluid/carrier gas mixture is constrained by the aperture array 120 and by the interior wall 138 such that the sample fluid/carrier gas mixture and the metastables are swept through the lower ionization chamber 116. The mixture and the detector gas is permitted to exit the lower ionization chamber 116 through the vents 126.

Another aspect of the illustrated embodiment is that the portion of the detector gas that flows through the upper ionization chamber 114 is rapidly moved downstream from the radioactive particle source 140, due to the pressure of the detector gas flow and the small internal diameter of the bores 128. This encourages good distribution and ionization of the analyte molecules in the lower ionization chamber 116, while minimizing the migration of gases, contaminants, sample molecules, and so on from the lower ionization chamber 116 into the upper ionization chamber 114.

What is claimed is:

1. An ionization detector for analysis of an analyte provided in a sample fluid, comprising:

an upper ionization chamber;

a radioactive particle source;

means for providing a fluid stream of detector gas to the upper ionization chamber so as to fill the upper ionization chamber with detector gas;

wherein the radioactive particle source is disposed on the periphery of the interior of the upper ionization chamber so as to generate a supply of radioactive particles into the internal volume defined by the upper ionization chamber, and wherein the interaction of the radioactive particles and the detector gas generates metastables and photons as the radioactive particles traverse a portion of the internal volume of the upper ionization chamber;

a lower ionization chamber coupled to the upper ionization chamber so as to receive the detector gas flow and the metastables;

means for directing the fluid mixture containing the analyte into the lower ionization chamber, whereby the metastables present in the lower ionization chamber ionize the analyte molecules; and a radioactive particle barrier interposed in the path between the radioactive particle source and the lower ionization chamber wherein the radioactive particle barrier limits the path of the emitted radioactive particles to the internal volume defined by the upper ionization chamber, so as to block the entry of the radioactive particles into the lower ionization chamber;

whereby the primary mechanism for ionization of the analyte molecules is substantially restricted to an interaction of the metastables with the analyte molecules.

2. The ionization detector of claim 1, further comprising an outlet provided in the lower ionization chamber so as to vent the combined flows of the carrier gas, sample fluid, and the detector gas.

3. The ionization detector of claim 1, wherein at least one of the carrier gas and the detector gas are selected from a group consisting of the noble gases.

4. The ionization detector of claim 1, further comprising an aperture array disposed between the upper ionization chamber and the lower ionization chamber.

5. The ionization detector of claim 1, wherein the carrier gas and the detector gas are helium.

6. The ionization detector of claim 1, wherein the radioactive particle source is provided in the form of an alpha particle emitter.

7. The ionization detector of claim 1, further comprising means for receiving the carrier gas flow supplied from an outlet end of a capillary separation column.

8. The ionization detector of claim 1, wherein the upper ionization chamber includes a high voltage ionization electrode coupled to a high voltage supply.

9. The ionization detector of claim 1, wherein the lower ionization chamber includes a high voltage signal cathode coupled to a high voltage supply, whereby a detector signal is generated.

10. The ionization detector of claim 1, wherein the lower ionization chamber includes injection port means for converting the ionization detector for use as an electron capture detector by injection of methane gas into the lower ionization chamber.

* * * * *